United States Patent [19]

Ford, Jr. et al.

[11] Patent Number: 4,640,440

[45] Date of Patent: Feb. 3, 1987

[54] FOAM DISPENSING DEVICE

[75] Inventors: George W. Ford, Jr.; Darrel R. Palmer, both of Sandy, Utah

[73] Assignee: Ballard Medical Products, Midvale, Utah

[21] Appl. No.: 722,831

[22] Filed: Apr. 12, 1985

[51] Int. Cl.⁴ .................. B67D 5/58; B65D 37/00
[52] U.S. Cl. .................. 222/190; 222/210; 222/211
[58] Field of Search ............... 222/190, 206–207, 222/209–213, 372, 394, 401, 464, 481, 481.5; 239/307–308, 327–328, 343, 345, 373, 432–433; 604/212

[56] References Cited

U.S. PATENT DOCUMENTS

| | | | |
|---|---|---|---|
| 3,012,695 | 12/1961 | Lerner | 222/129 |
| 3,422,993 | 1/1969 | Boehm et al. | 222/190 |
| 3,618,846 | 11/1971 | Poli | 222/206 X |
| 3,622,049 | 11/1971 | Thompson | 222/190 |
| 3,651,990 | 3/1972 | Cernei | 222/94 |
| 3,709,437 | 1/1973 | Wright | 239/343 |
| 3,938,514 | 2/1976 | Boucher | 128/232 |
| 4,024,992 | 5/1977 | Schmid | 222/211 |
| 4,327,782 | 5/1982 | McKibben et al. | 141/26 |
| 4,349,129 | 9/1982 | Amneus | 222/206 X |
| 4,411,656 | 10/1983 | Cornett, III | 604/212 |
| 4,516,697 | 5/1985 | Dreps et al. | 222/212 |
| 4,531,659 | 7/1985 | Wright | 222/190 |

FOREIGN PATENT DOCUMENTS 7723 of 1895 United Kingdom ............... 222/401

Primary Examiner—Joseph J. Rolla
Assistant Examiner—Michael S. Huppert
Attorney, Agent, or Firm—Lynn G. Foster

[57] ABSTRACT

The foam dispensing device is intended for use in the inverted position and includes a container having a reservoir portion for holding a foamable liquid and a bellows portion for holding air. A foam producing unit is mounted in the discharge port, the foam producing unit including a housing mounted in and receiving air from the bellows and a liquid receiving conduit extending from the foam producing unit into the reservoir. A separate air return conduit communicating with atmosphere extends into the container air. The container reservoir and bellows portions are separated by a finger-engageable waist portion to facilitate operation of the bellows portion.

5 Claims, 10 Drawing Figures

FOAM DISPENSING DEVICE

BACKGROUND OF THE INVENTION

This invention relates generally to non-aerosol, foam dispensing devices and particularly to a foam dispensing device which is used in the inverted position.

Foam dispensing devices of the type under consideration have been known for at least fifteen years and are represented by U.S. Pat. No. 3,422,993 issued to G. L. Boehm; U.S. Pat. No. 3,709,437 issued to H. E. Wright; U.S. Pat. No. 3,622,049 issued to R. E. Thompson and U.S. Pat. No. 4,024,992 issued to Schmid. Of these patents the Boehm and Wright disclosures are believed most pertinent and show devices that can be used in the inverted condition. Boehm makes no specific provision for air return and Wright provides a valved air return system in the foam discharge conduit. The Thompson patent discloses a separate air return system but cannot be used in the inverted position. One other known foam dispensing device manufactured by Ballard Medical, Inc., the assignee of the present invention provides a separate air return conduit which extends into the container air space when the container is inverted. However, the foam producing means is under liquid head during operation which leads to undesirable migration of unfoamed liquid through the spout when the device is inverted. In addition, such devices in general use a conventional squeeze container which is of limited effectiveness in dispensing the foam.

The present invention solves the above described problems in a manner not disclosed in the known prior art.

SUMMARY OF THE INVENTION

This foam producing device includes a separate air return system which facilitates the return of air into the container an improved liquid delivery system supplying liquid and air to the foam producing unit mounted within the container and a container configuration which facilitates the application of pressure and the production of foam.

The separate air return system permits the use of a relatively large air return conduit, and a use of a long nozzle for insertion into body cavities, the air return being located independently of the nozzle and outside of the body cavity. This advantageous feature is useful in expediting surgical techniques by facilitating vaginal preparation for example.

The device also provides a liquid delivery system which is oriented during the foaming operation to provide an anti-syphoning effect to minimize leakage.

The container is particularly adapted for single-handed manual application of pressure.

The foam dispensing device includes a unitary container for holding foamable liquid and air having a discharge port, a reservoir portion disposed adjacent the discharge port, a bellows portion remote from the discharge port and a finger engageable portion disposed between said bellows portion and said reservoir portion; means associated with the container having air inlet means and foam outlet means; foam producing means associated with the container and means communicating with the reservoir portion and the bellows portion; means communicating between the foam producing means and the foam outlet means; means communicating between the air inlet means and the container air space, and valve means closing the air inlet means when pressure is applied to the bellows portion and opening the air return means when pressure applied to the bellows portion is relieved.

It is an aspect of this invention to provide that the finger engageable portion disposed between the reservoir portion and the bellows portion is reduce in diameter to provide a waist portion.

It is another aspect of this invention to provide that the bellows portion and the reservoir portion are substantially the same diameter. It is yet another aspect of this invention to provide that the foam producing means is disposed in the bellows portion when the container is in the inverted condition.

It is still another aspect of this invention to provide that an elongate liquid conduit communicates with the foam producing means having a liquid receiving opening disposed to receive liquid from the container; the means communicating between the foam producing means and the foam outlet means includes an elongate conduit and the means communicating between the air inlet means and the container air space contains an elongate air return conduit.

It is another aspect of this invention to provide that the foam producing means includes a housing providing a mixing chamber receiving liquid from the liquid conduit and having an air entry aperture.

DESCRIPTION OF THE PREFERRED EMBODIMENT

Figure 1:
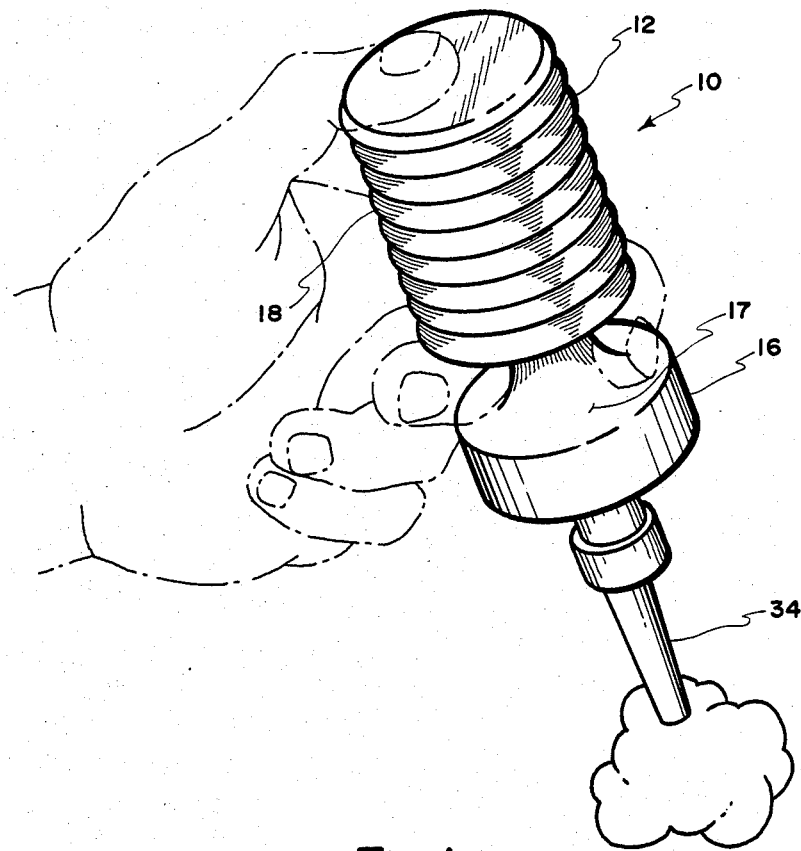
FIG. 1 is a perspective view of the foam dispensing device in the inverted, use position.
Figure 2:
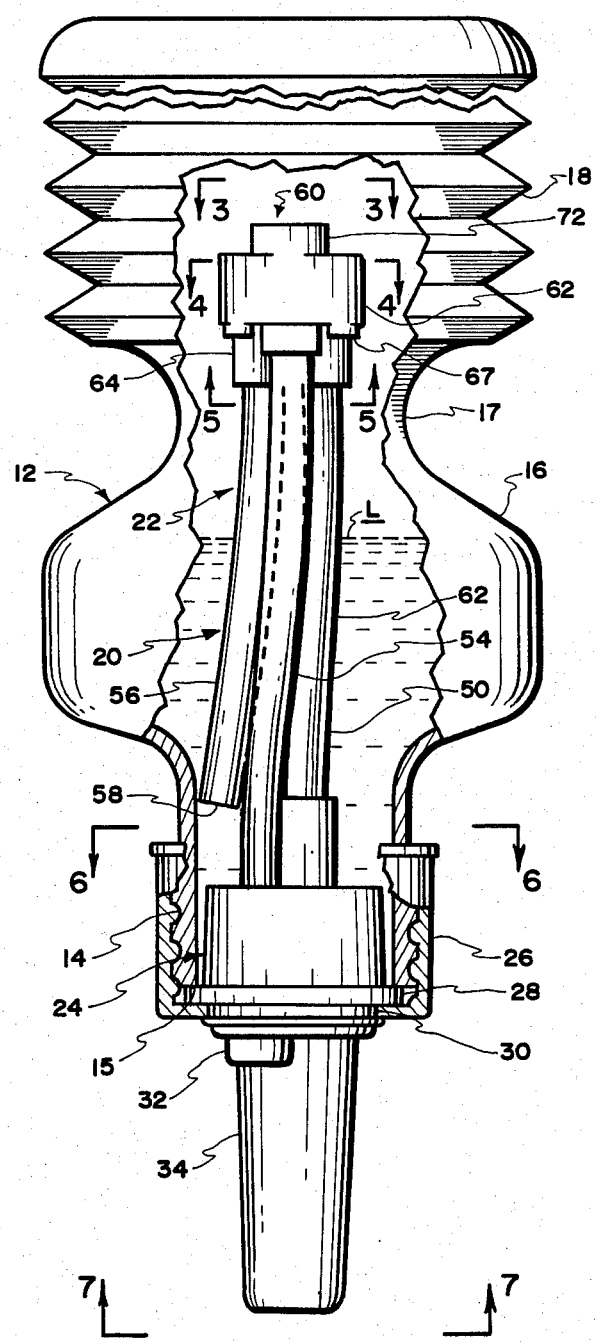
FIG. 2 is an elevational view of the device partly in cross section.

Referring now by reference numerals to the drawings and first to FIG. 1 it will be understood that the foam dispensing device, generally indicated by numeral 10, includes a container 12. The container is in the nature of a plastic squeeze bottle having a neck portion 14 defining a discharge port, a first body portion defining a reservoir 16 and a second body portion defining a bellows pump 18 which is separated from the reservoir portion by a waist portion 17. As shown in FIG. 2, the foam dispensing device 10 also includes a foam producing unit generally indicated by numeral 20 which is mounted to the container and consists essentially of a foam producing system 22 and a closure 24. In the embodiment shown the foam producing unit 20 is held in place by a cap 26 which is attached to and forms part of the closure 24. To this end, the closure 24 includes an annular flange 28 engageable with the end 15 of the container neck 14 and an adjacent groove 32 receiving the cap 26.

The component parts of the closure 24 and the foam producing system 22, which are formed from molded plastic material, will now be more specifically described.

Figure 8:
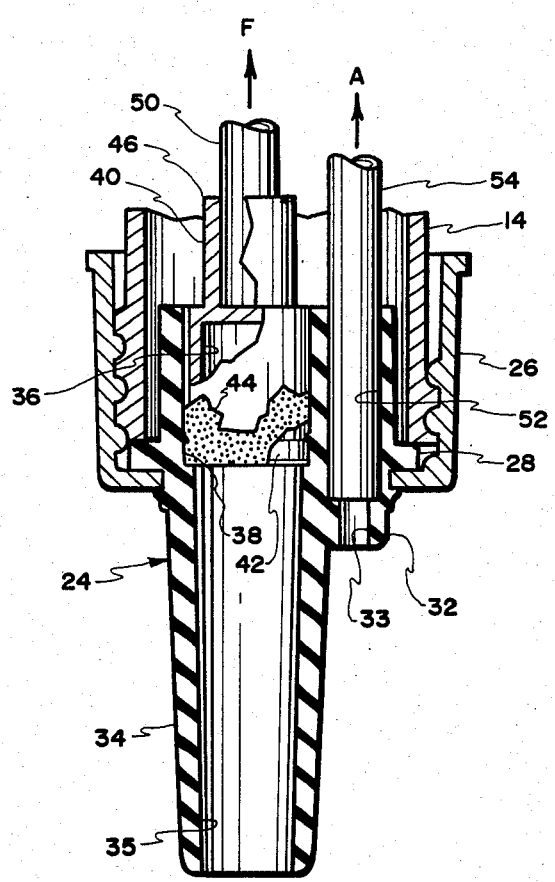
FIG. 8 is a fragmentary longitudinal cross section taken on line 8—8 of FIG. 7.

As shown in FIG. 8, the closure 24 includes a tubular portion 32 providing a passage 33, constituting an air inlet means, and a relatively long spout 34 having a passage 35 constituting a foam outlet means. The closure member 24 also includes an enlarged diameter passage 36 communicating with the spout passage 35 and defining a groove 38. The passage 36 receives an adaptor member 40 having a flange 42 at the remote end which interfits the groove 38 to provide a means of holding a gauze filter 44 in place over the end of the adaptor member 40, said gauze filter constituting a diffusion or homogenizing means for refining the foam bubbles passing into the spout 34. The adaptor member 40 includes a reduced diameter inner portion 46 receiving a tubular member 50 providing a foam discharge conduit. The closure member 24 also includes an inwardly extending passage 52 which communicates with the passage 33 providing the air inlet means and said passage 52 receives a tubular member 56 providing a return air conduit.

As shown in FIG. 2 the tubular members 50 and 54 both communicate with a foam producing head 60. A third tubular member 56, having an end opening 58, receiving liquid L from the container reservoir 16, when the container 12 is inverted, also communicates with the foam producing head 60. The foam producing head 60 will now be described in greater detail with reference to FIGS. 2-5, 9 and 10.

Figure 3:
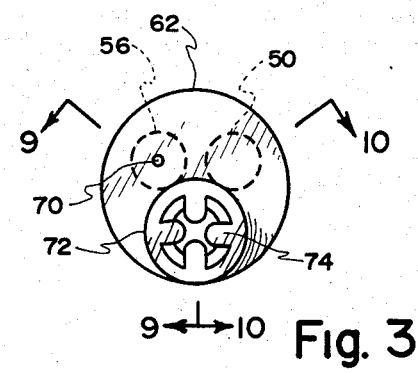
FIG. 3 is an end view of the foaming unit taken on line 3—3 of FIG. 2.
Figure 5:
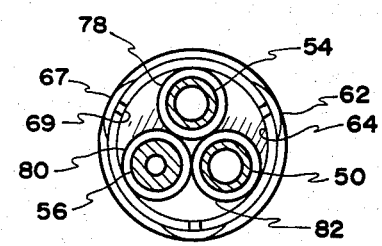
FIG. 5 is a cross sectional view taken on line 5—5 of FIG. 2.
Figure 6:
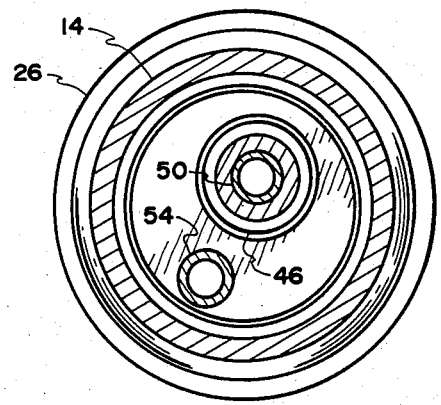
FIG. 6 is a cross sectional view taken on line 6—6 of FIG. 2.
Figure 7:
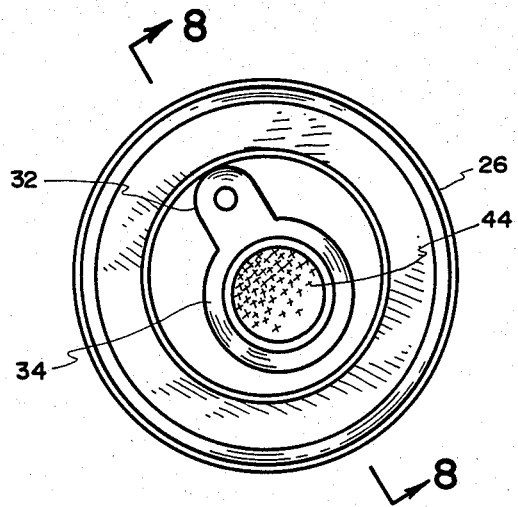
FIG. 7 is an end view of the device taken on line 7—7 of FIG. 2.
Figure 9:
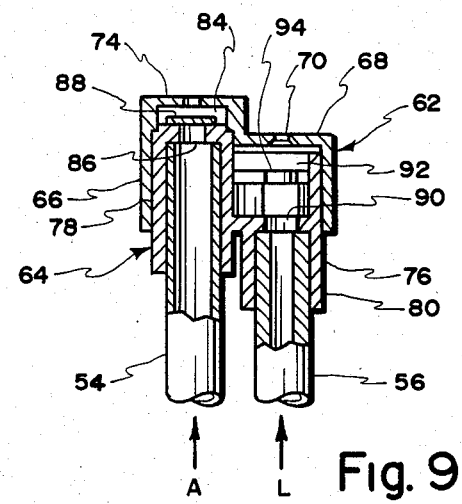
FIG. 9 is a fragmentary longitudinal sectional view taken on line 9—9 of FIG. 3.
Figure 10:
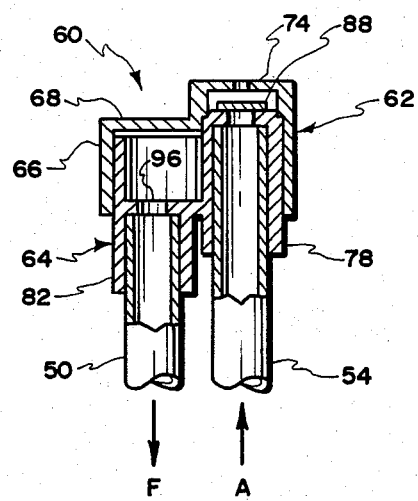
FIG. 10 is a fragmentary longitudinal sectional view taken on line 10—10 of FIG. 3.

The foam producing head 60 in the embodiment shown is formed from an outer casing member 62 and an interfitting, inner insert member 64 both of generally circular configuration. As shown in FIG. 9, the casing member 62 includes a sidewall 66 and an end wall 68 provided with an air inlet opening 70. As shown in FIG. 3, the casing member 62 also includes an offset tubular portion 72 having an endwall formed into a plurality of retaining fingers 74 defining an air return opening. As shown in FIGS. 9 and 10, the insert 64 includes a sidewall 76 interfitting the casing sidewall 66 and having integrally formed tubular portions 78, 80 and 82. As shown in FIGS. 2 and 5, casing sidewall 66 includes lugs 67, having inwardly projecting elements 69 engageable with the underside of insert sidewall 76 to hold said casing and insert together.

Figure 4:
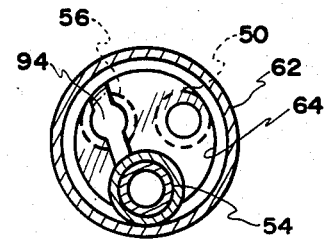
FIG. 4 is a cross sectional view taken on line 4—4 of FIG. 2.

As best shown in FIGS. 9 and 10 the insert tubular portion 78 is received into the casing offset tubular portion 72 and receives the end of the air return tubular member 54. The tubular portion 54 includes an end aperture 86 and said tubular portions 72 and 78 cooperate to define a valve chamber 84 having a disc check valve element 88. The disc element is movable between a closed position blocking air flow into the air return member 54 and an open position against the fingers 74 to permit air return from the air return member 54 into the container air space defined by the bellows 18. As best shown in FIG. 9 the tubular portion 80 receives the end of the liquid supply conduit member 56 and includes an aperture 90 opening into a foam chamber generally indicated by numeral 92. Air entry aperture 70 and liquid entry aperture 90 are generally aligned and a deflector element 94 is disposed in the path of the air stream and liquid stream entering the foam chamber 92. As shown in FIGS. 4 and 9, the deflector is supported at its ends and is, in the embodiment shown of somewhat larger diameter than the inside diameter of the tubular member 56. As best shown in FIG. 10 the tubular portion 82 receives the end of the foam discharge conduit member 50 and includes an aperture 96 communicating with the foam chamber 92 to receive foam formed in said chamber.

In the embodiment shown the reservoir 16 is of a size to accomodate about 2½ fluid ounces of liquid. The tubular members 50, 54 and 56 are of the same outside diameter, namely 0.184 inches ±0.007 inches. However, while the inside diameter of foam discharge conduit member 50 and the return air conduit member 56 are substantially the same at 0.134 inches ±0.002 inches, the inside diameter of the liquid conduit member is considerably smaller at 0.068 inches ±0.002 inches.

In the embodiment shown the diameter of the air entry opening is 0.010 inches ±0.002 inches.

It is thought that the functional advantages and structural features of this foam dispenser have become fully apparent from the foregoing description of parts but for completeness of disclosure the operation of the device will be briefly described.

The foam dispenser 10 is intended for operation in the inverted position such that the foam head 60 is disposed in the air space provided by the bellows 18 while the liquid entry opening 58 of the tubular member 56 is disposed at a relatively low elevation in the container reservoir 16. As shown in FIGS. 1 and 2, the container 12 includes an inwardly formed relatively small diameter waist portion between the bellows 18 and the reservoir 16 which conveniently receive the index finger and the middle finger of the operator so that the thumb can readily depress the flexible bellows 18 of the squeezable container 12.

As best understood by FIGS. 2, 9 and 10, upon depression of the bellows 18 liquid L is forced into the tubular member 56 below the liquid surface while air is forced into the air inlet aperture 70 above the liquid surface. Air is also forced into the valve chamber 84 forcing the check valve disc 88 into the position shown in FIG. 9 to effectively close the return air tubular member 54. The air stream and liquid stream entering the foam chamber 80 impinge on the deflector member 94 to form foam which is discharged through aperture 90 and into foam discharge member 50. The foam passes through the homogenizing gauze filter element, which reduces the large bubbles, and into the spout 34 from which it is discharged as a high quality foam.

Upon release of the thumb the bellows returns to its original position creating a suction force lifting the valve disc 88 away from the return air entry aperture 86 and drawing air into the bellows 18 of the container 12.

The arrangement of the liquid conduit tubular member 54 in the position shown provides an effective antisyphoning device in that liquid retained in the tubular member 56 following pressure release tends to seek the level of the liquid in the container 12. Only residual foam remains in the tubular member 50 and this is held by the diffusing filter. Thus liquid drip from the device is eliminated.

In view of the above, it can be seen that the various aspects and features are achieved and other advantageous results obtained. While two preferred embodiments of the present invention have been described, it should be understood that various changes, adaptations, and modifications may be made therein without departing from the spirit of the invention and the scope of the appended claims.

We claim as our invention:

1. A foam dispensing device for use in an inverted condition, comprising:
   (a) an hour glass-shaped one piece container for holding foamable liquid and air having a discharge port, a reservoir portion disposed at one end of the container adjacent the discharge port, a bellows portion disposed at the other end of the container remote from the discharge port and a necked-down finger engageable portion centrally disposed between said bellows portion and said reservoir portion, said central finger engageable portion being substantially reduced in its transverse area when compared to the reservoir portion and the bellows portion,
   (b) means associated with the container having air inlet passage means and foam outlet passage means, whereby air is selectively admitted into the interior of the device and foam is selectively extruded from the interior of the device,
   (b1) means communicating with the reservoir portion and the bellows portion,
   (c) foam producing means associated with the container and said means communicating with the reservoir portion and the bellows portion,
   (d) means communicating between the foam producing means and the foam outlet means,
   (e) means communicating between the air inlet means and the container air space, and
   (f) valve means closing the air inlet means when pressure is applied to the bellows portion and opening the air return means when pressure applied to the bellows portion is relieved.

2. A device as defined in claim 1, in which:
   (h) the bellows portion and the reservoir portion are substantially the same diameter.

3. A device as defined in claim 1, in which:
   (g) the foam producing means are disposed in the bellows portion and are operable when the container is in the inverted condition.

4. A device as defined in claim 3, in which:
   (h) an elongated liquid conduit communicates liquid from the reservoir portion to the foam producing means, disposed above the reservoir portion within the bellows portion, when the device is inverted, the foam producing means having a liquid receiving opening disposed to receive liquid from the elongated liquid conduit,
   (i) the means communicating between the foam producing means and the foam outlet means includes an elongated conduit, and
   (j) the means communicating between the air inlet means and the container air space includes an elongate air return conduit.

5. A device as defined in claim 2, in which:
   (i) the foam producing means include a housing providing a mixing chamber receiving liquid from the liquid conduit and having air entry aperture means.

* * * * *